United States Patent [19]

Chorbajian

[11] Patent Number: 4,557,692

[45] Date of Patent: Dec. 10, 1985

[54] OCCLUSAL SPLINTS AND THE METHOD OF MANUFACTURING THE SAME

[76] Inventor: Peter M. Chorbajian, 10004 Carter Rd., Bethesda, Md. 20034

[21] Appl. No.: 489,602

[22] Filed: May 2, 1983

Related U.S. Application Data

[63] Continuation of Ser. No. 233,725, Feb. 12, 1981, abandoned.

[51] Int. Cl.⁴ ............................................... A61C 5/00
[52] U.S. Cl. .................................................. 433/215
[58] Field of Search ........................ 433/215, 225, 167

[56] References Cited

U.S. PATENT DOCUMENTS 4,384,854  5/1983  Garfinkel .
4,433,960  2/1984  Garito .

*Primary Examiner*—Robert Peshock
*Attorney, Agent, or Firm*—John J. Byrne; Bradford E. Kile; Kevin M. O'Brien

[57] ABSTRACT

Disclosed are occlusal splints and the method of manufacturing the same. The occlusal splints described are worn on the upper arch of the mouth over the teeth. They are formed of two layers. The first layer is formed of a soft material molded to conform to the shape of the upper teeth and to be resiliently retained thereon, and the second layer is made of cold-cure acrylic resin built up on the first layer.

3 Claims, 11 Drawing Figures

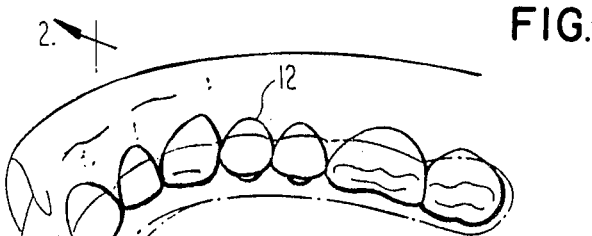
FIG. 1
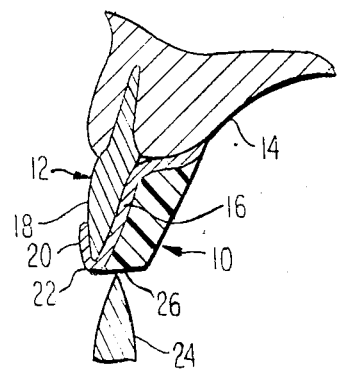
FIG. 2
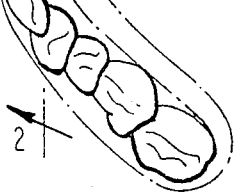
FIG. 3
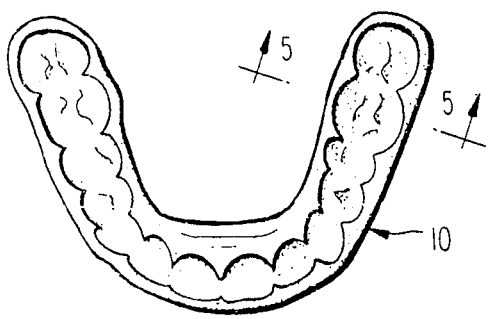
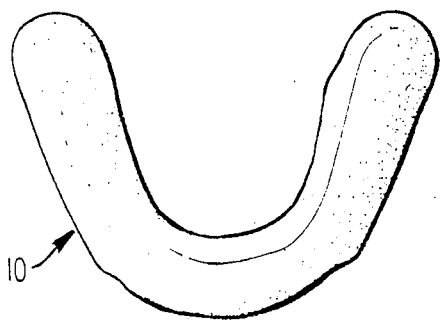
FIG. 4
FIG. 5
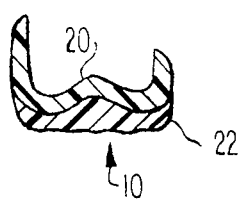
FIG. 6
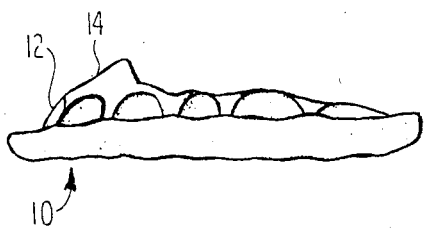

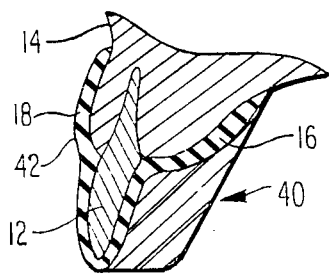
FIG. 7
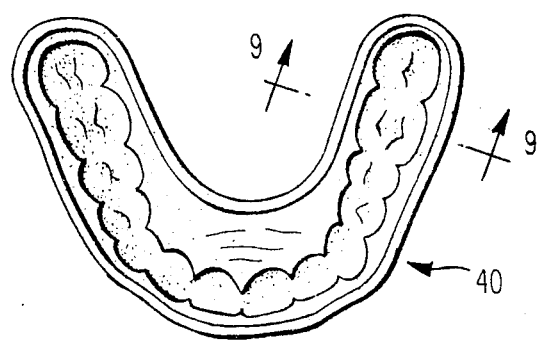
FIG. 8
FIG. 9
FIG. 11
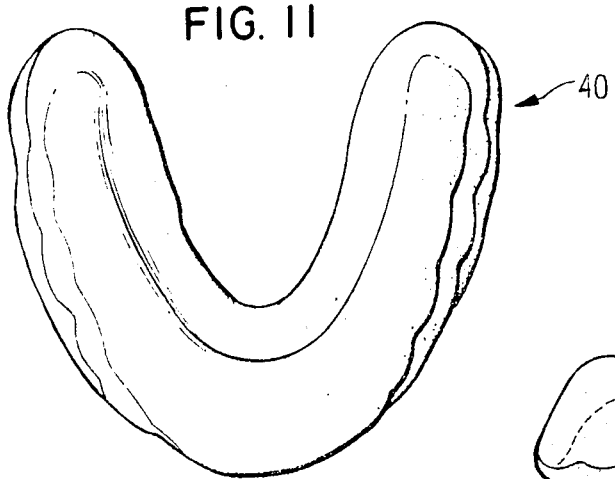
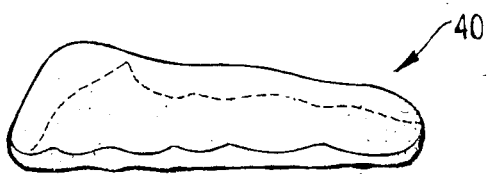
FIG. 10

OCCLUSAL SPLINTS AND THE METHOD OF MANUFACTURING THE SAME

This application is a continuation, of application Ser. No. 233,725, filed Feb. 12, 1981, now abandoned.

TECHNICAL FIELD

This invention relates to occlusal splints and to methods of manufacturing occlusal splints.

BACKGROUND OF THE INVENTION

Some occlusal splints are used as diagnostic and repositioning tools. They are worn until the patient has had a proper occlusal diagnosis and evaluation after a clinical examination of the complete gnathostomatic system before a permanent (and irreversible) program is undertaken to change the occlusion. In this capacity, occlusal splints serve as a reversible procedure to confirm an occlusal diagnosis and to temporarily relieve the symptoms of malocclusion and tempromandibular joint dysfunction.

Other occlusal splints are used to relieve strain and tension, particularly in athletes. Such splints are typically formed from a sheet of resin which is shaped to follow the surface of the teeth. Thus, the distal surface of the splint has a shape which closely approximates the shape of the teeth over which the splint is worn.

Still other occlusal splints are worn simply as cushioning. Such splints are also commonly worn by athletes, particularly athletes involved in contact sports, such as football and boxing, and they are made of a soft, "chewy" material known as "mouthguard material."

BRIEF SUMMARY OF THE INVENTION

The occlusal splint according to this invention has an outside surface (i.e., the surface which contacts the lower teeth) formed of a relatively hard, non-resilient material which is shaped so that all the lower posterior teeth strike the splint at the same time, equalizing the pressure on each lower posterior tooth. The upper portion of the splint (i.e., the portion next to the teeth and palate) is formed of a resilient material which extends above the greatest curvature of at least some of the upper teeth, permitting the splint to be retained resiliently on the upper teeth by a "snap fit."

ADVANTAGES OF THE INVENTION

An occlusal splint according to this invention measures the degree of closure and allows the brain to reprogram the mandible to any position of closure that will be completely acceptable and will afford maximum comfort without straining or stressing the musculature of the gnathostomatic system. It does not add power, but it does release strength which the wearer already has but which is tied up by stress due to the wearer's teeth not being properly aligned.

One may have tempro-mandibular joint dysfunction without being aware of it. Such dysfunction, when due to a lack of balance between the upper and lower teeth, exhausts muscle strength by loss of tonus, causing fatigue and pain. Soon other muscles are used to perform the function of muscles that are already exhausted. As a result, there is a general strain of all of the musculature. However, an occlusal splint according to this invention substantially alleviates, and sometimes eliminates, tempro-mandibular joint dysfunction.

BRIEF DESCRIPTION OF THE DRAWINGS

FIG. 1 is an isometric view looking upwardly towards a first embodiment of an occlusal splint according to this invention in position on the upper teeth or on a mold of the upper teeth. The occlusal splint is shown in broken line in order to clearly show its relationship to the teeth.

FIG. 2 is a cross-sectional view on a larger scale along the line 2—2 in FIG. 1.

FIG. 3 is a top plan view of the occlusal splint shown in FIG. 1.

FIG. 4 is a bottom plan view of the occlusal splint shown in FIG. 1.

FIG. 5 is a cross-sectional view along the line 5—5 in FIG. 3.

FIG. 6 is a side view of the occlusal splint in position on the upper teeth or on a mold of the upper teeth.

FIG. 7 is a view similar to FIG. 2 of a second embodiment of an occlusal splint according to this invention.

FIG. 8 is a top plan view of the occlusal splint shown in FIG. 7.

FIG. 9 is a view along the line 9—9 shown in FIG. 8.

FIG. 10 is a side view of the occlusal splint shown in FIG. 8 in position on the upper teeth or on a mold of the upper teeth.

FIG. 11 is a bottom plan view of the occlusal splint shown in FIG. 7.

DETAILED DESCRIPTION OF THE INVENTION

First Embodiment

The occlusal splint 10 shown in FIGS. 1-6 is adapted to be worn on the upper arch of the mouth over the upper teeth 12 substantially twenty-four hours a day—that is, at all times except when the patient is eating. As best seen in FIGS. 2 and 5, when it extends upwardly to the palate gums 14 and the lingual (or inside) surface 16 of the teeth 12, but does not do so on the labial (or outside) surface 18 of at least the anterior, or front, teeth. However, the fact that the splint does not extend as far up towards the gums 14 on the labial surface 18 is for cosmetic rather than functional reasons, and the splint can extend upwardly to the gums 14 on the surface. In any event, as shown in FIG. 1, the splint 10 extends above the greatest curvature of at least some of the upper teeth 12 (namely, the pre-molars and molars) on both sides.

The splint 10 is formed of two layers of resin, preferably acrylic resin. The first, or inside, layer 20 is molded to conform to the shape of the upper teeth. It is made from an acrylic resin sheet of uniform thickness, so the lower surface of the upper layer 20 closely approximates the shape of the teeth over which the splint is worn, as is the case with conventional splints. However, the second, or outside, layer 22 represents a radical departure from conventional splints. The outside layer 22 is made of cold-cure acrylic resin built up on the first layer 20. As is explained in detail hereinafter, the outside surface of the outside layer 22 is shaped so that all the lower posterior teeth strike the splint at the same time, equalizing the pressure on each lower posterior tooth. Since the upper portion of the splint 10 is formed of a resilient material, the splint is retained resiliently on the upper teeth by a "snap fit."

The first step in preparing an occlusal splint according to this invention is to make a model of the upper arch by conventional techniques. The model is sprayed with an even coat of silicone mold release—preferably Crown 2 silicone mold release. Care is exercised in this step, since over-mold spraying causes undesirable side affects in the finished splints and underspraying causes sticking between the model and the splint.

Next, a moldable resin splint blank (preferably formed of acrylic resin 0.080 or 0.100 inches thick) is heated until it becomes pliable. While the splint blank is pliable from the heat, it is formed to the model. This is done in a Microform press using 90 lbs./sq. in. pressure.

The splint blank is allowed to cool. It is then cut on the buccal surface slightly above the greatest curvature of the bicuspid and molar teeth and approximately 2 mm above the incisal edge of the anterior teeth. The cut extends in a continuous, smooth line from the distal surface of the most posterior molar on one side to the distal surface of the most posterior molar on the other side. This can be accomplished, for example, using a #703 long shank burr in a straight low-speed handpiece. No portion of the palatal area is removed at this time.

After cutting, the splint blank is removed from the model by prying at the posterior border, thereby removing the formed splint blank in an anterior direction. A beavertailed wax instrument may be used as a lever. The reason for removing the splint blank from the model back to front, rather than vice-versa, is to avoid the fracturing of teeth on the model and, more importantly, to avoid distortion of the splint blank as it is removed from the model.

The uppermost palatal area of the splint blank is then removed behind a line connecting a point lingually spaced from the cervical line of the most posterior tooth on one side, a point lingually approximately 15 mm from the cervical line of the anterior teeth, and a point lingually spaced from the cervical line of the most posterior tooth on the other side. This is accomplished by drawing a continuous, smooth line connecting these three points using an indelible pencil and then cutting away the splint blank outside the line using a #703 long shank burr in a straight low-speed handpiece.

Next, the margin of the splint blank is made smooth, as with an acrylic burr, and a trial fit of the splint blank in the patient's mouth is made to check for irregularities. The splint blank is then removed from the patient's mouth, and the lingual surface over all the teeth and the occlusal surface over the bicuspid and molar teeth are scarified to promote adherence thereto of the cold-cure resin which is built up thereon in subsequent steps. The scarification may be done with a long shank green stone.

At this point the patient's mandible is exercised manually and closed against the upper jaw in a manner so that the condyle on each side is in the most retruded rest position of the glenoid fossa of the temporal bone on each side, which is termed to be a centric relation. The patient is asked to bite on two cotton rolls anteriorly to maintain the relation of the lower jaw to the upper jaw.

The cotton rolls are then removed, the patient's lower anterior teeth are lubricated with a thin film of petroleum jelly, and the anterior portion of the scarified splint blank is wetted with a liquid component of a cold-cure resin (preferably cold-cure acrylic resin). A portion of dough-like cold-cure resin then is placed on the rugae area of the splint blank behind the anterior teeth and flattened over the anterior portion of the splint blank to the contour of the anterior palate, and the formed splint blank is placed on the patient's upper teeth. While the cold-cure resin is still pliable, the mandible is closed in centric relation. The patient at this time is guided to closure until a slight contact is made between his or her anterior lower teeth 24 and an apron 26 of the previously emplaced soft, pliable resin behind the upper anterior teeth 18 (see FIG. 2). This slight contact leaves an impression of the anterior teeth called an index in the resin. During this step care is exercised to ensure that a clearance of at least approximately 2 mm is maintained between the formed splint blank over the most posterior area of the upper molar teeth and the corresponding most posterior area of the lower molar teeth.

Next, after the cold-cure resin has begun to harden but before it becomes painfully hot due to the exothermic reaction between the acrylic monomer and the acrylic polymer, the assembly comprising the splint blank and the built-up resin on the anterior portion of the splint blank is removed from the patient's mouth. Two cotton rolls placed over each other are again inserted between the anterior teeth to prevent the patient from moving the condyles out of the most retruded rest positions of the glenoid fossae of the temporal bones, and the patient is asked to close in a natural bite—not an edge-to-edge closing. After the cold-cure resin has hardened, it is reduced to the deepest depth of the impressed index, until only one lower anterior tooth contacts only one point on the indexed surface. The remainder of the newly hardened cold-cure resin is shaped to the form of the palate, providing room for the patient's tongue. This is accomplished using an acrylic burr.

The cotton rolls are then removed from the patient's mouth, and the splint is re-positioned on the upper teeth. The patient is asked to hold marking ribbon between the splint and his or her lower teeth, and the mandible is moved from centric relation to a forward position, then back, then to one side, back, then to the other side, and back. These movements are repeated several times before the splint is removed. After the splint is removed, fresh cotton rolls are again inserted between the patient's anterior teeth to prevent him or her from moving his or her condyles out of the most retruded rest position of the glenoid fossae of the temporal bones, and the patient is asked to close his or her teeth in a natural bite as before.

Any eccentric marks found on the hardened cold-cure acrylic are removed at this time. The only point of contact is made now by only that single lower anterior tooth with the jig of the splint at one point only. This procedure permits the jaw muscles to be reprogrammed so that the mandible attains a natural centric relation because the lower teeth slide across the smooth lower surface of the splint until the lower tooth which made the deepest index comes to rest against the remaining portion of that index, which has previously been established as defining the centric relation.

The splint is then removed, and the patient's lower posterior teeth (i.e., his or her bicuspid and molar teeth) are lubricated with a thin film of petroleum jelly. Cotton rolls are again placed between the anterior teeth. The bicuspid and molar areas of the scarified splint blank are wetted with a liquid component of a cold-cure resin (preferably, the same cold-cure acrylic resin), after which portions of dough-like cold-cure resin are placed over the wetted bicuspid and molar areas on both sides of the splint blank. The cotton rolls are then removed from between the patient's teeth, and the formed splint blank is placed on the patient's upper teeth. While the cold-cure resin is still pliable, the mandible is again positioned in closed centric relation, the centric relation now being determined by contact between the lower anterior tooth which made the deepest depression in the cold-cure resin previously emplaced and the remaining portion of that index. The contact between the posterior lower teeth and the soft, pliable resin over the posterior upper teeth leaves indices in the resin, as before.

After the cold-cure resin has begun to harden but before it becomes painfully hot due to the exothermic reaction between the acrylic monomer and the acrylic polymer, the assembly comprising the splint blank, the hardened cold-cure resin on the anterior portion of the splint blank, and the still pliable cold-cure resin on the posterior portion of the splint blank is removed from the patient's mouth. Two fresh cotton rolls are inserted between his or her anterior teeth to prevent him or her from moving his or her condyles out of the most retruded rest position of the glenoid fossae, and the patient is asked to close his or her teeth in a natural bite as before.

After the cold-cure resin on the posterior portion of the splint blank has hardened, the indices in the posterior portion of the splint blank are marked. This may be done using black Liqua Mark marking fluid which is dried after application with an air syringe. The resin surrounding the indices made in the posterior portion of the splint by the posterior lower teeth is then removed until only small dots on the order of 0.5 mm in diameter remain where the cusp tips of the bicuspids and molars made the deepest depressions in the pliable resin. It should be particularly noted that, in contrast to the comparable step involving the indices made by the lower anterior teeth, the deepest portions of the indices made by the cusp tips of all of the lower posterior teeth are allowed to remain in the splint. This step is also accomplished with an acrylic burr.

Any excess hardened cold-cure resin is then removed from the lingual, buccal, and occlusal surfaces of the splint, taking care, of course, to leave the previously mentioned single index for one of the lower anterior teeth and the multiple indices of the lower posterior teeth. This step, too, is accomplished using an acrylic burr.

Next, the hardened cold-cure resin extending back over the palate is trimmed away, since it is no longer needed for ease of handling, leaving the splint in a shape resembling a horseshoe. This is accomplished using a #703 long shank burr in a straight low-speed handpiece.

Eccentric contacts (i.e., places where the lower teeth would bump into the splint when the mandible is moved from side to side) in the anterior lingual area are then removed to develop the lingual concavity. This step is also accomplished using a #703 long shank burr in a straight low-speed handpiece.

Next, the exterior surface of the splint is smoothed, for instance with the use of an acrylic burr, while carefully preserving the remaining 0.5 mm portions of the indices in the splint.

Finally, the exterior surfaces of the occlusal splint are finished, for instance with pumice and Final Lustre finishing compound, and the finished splint is positioned in the patient's mouth.

It should be noted that occlusal splints made by the foregoing process, like all occlusal splints, can be worn only for a restricted period of time before they lose their efficacy due to wear of the surfaces which contact the lower teeth. They should be worn only until the patient has had a proper occlusal diagnosis and evaluation after a clinical examination of the complete gnathostomatic system. After such a complete occlusal diagnosis and evaluation has been accomplished, a permanent, irreversible program can be undertaken to change the patient's occlusion.

Occlusal splints made by the foregoing process may be used (1) as a diagnostic and repositioning tool and (2) as a temporary strain-reliever for patients in high tension situations. In the former situation, use of the splint serves as a reversible procedure to confirm an occlusal diagnosis and to temporarily relieve the symptoms of malocclusion and tempro-mandibular joint dysfunction. In the latter situation, while individual splints will lose their efficacy due to wear, replacement splints can be made and the use of such splints continued indefinitely.

Second Embodiment

The occlusal splint 40 shown in FIGS. 7-11 is similar to the occlusal splint 10 shown in FIGS. 1-6 except that it is specifically adapted to be worn in situations where forceful contact (as from body-contact sports) is anticipated by the wearer. Thus, this occlusal splint is not ordinarily worn twenty-four hours per day, as is the first embodiment. The second embodiment is also adapted to be worn on the upper arch of the mouth over the upper teeth 12, and it is also formed of two layers. However, the first, or upper, layer 42 is preferably formed of polyurethane mouthguard material rather than acrylic resin. It is also molded to conform to the shape of the upper teeth 12 and to be resiliently retained thereon, but, as best seen in FIGS. 7 and 9, it extends upwardly to the gums 14 on both the lingual surface 16 and the buccal surface 18 of at least the front teeth. Thus, the splint 40 also extends above the greatest curvature of at least some (and preferably all) of the upper teeth 12, and, since the upper portion of the splint 40 is also formed of a resilient material, the splint 40 is also retained resiliently on the upper teeth 12 by a "snap fit."

The second embodiment can be made by the same technique as the first embodiment except (1) a blank made of 0.150 or 0.200 rubber or a similar mouthguard material is substituted for the thinner blank of acrylic resin, (2) the molded splint blank is removed from the model of the upper arch by reversing it, rather than by prying it off, since it is considerably more resilient than the molded acrylic splint blank, (3) the trimming steps can be accomplished using small scissors rather than a #703 long shank burr, since the mouthguard material is easier to cut than the acrylic resin, and (4) the posterior palatal area of the splint may or may not be removed, depending on the patient's tolerance of a foreign body in contact with the roof of his or her mouth.

Caveat

While the present invention has been illustrated by a detailed description of two preferred embodiments thereof, it will be obvious to those skilled in the art that various changes in form and detail can be made therein without departing from the true scope of the invention. For that reason, the invention must be measured by the claims appended hereto and not by the foregoing preferred embodiments.

What is claimed is:

1. A method of making an occlusal splint having two layers of of resin material sized and shaped to be worn on the upper arch of the mouth over the teeth comprising the steps of molding an upper layer of resilient resin material to conform to the shape of the upper teeth and to be retained thereon, forming a lower layer of a cold-cure resin material which is built up on the upper layer, and shaping the lower surface of the lower layer so that the lower surface of the splint engages the upper surface of the lower teeth at a time when the condyls of the wearer are in their retruded rest position and said areas of engagement are all below the plane of the lowermost edges of said upper teeth.

2. The method of claim 1 wherein said upper resilient layer extends above the greatest curvature of at least some of the upper teeth.

3. The method of claim 1 wherein said upper layer is formed of acrylic resin.

* * * * *